(12) United States Patent
Juettner et al.

(10) Patent No.: US 10,857,241 B2
(45) Date of Patent: Dec. 8, 2020

(54) THERAPEUTICAL TOOLS AND METHODS FOR TREATING BLINDNESS BY TARGETING PHOTORECEPTORS

(71) Applicant: Friedrich Miescher Institute for Biomedical Research, Basel (CH)

(72) Inventors: Josephine Juettner, Basel (CH); Dasha Nelidova, Basel (CH); Botond Roska, Oberwill (CH)

(73) Assignee: FRIEDRICH MIESCHER INSTITUTE FOR BIOMEDICAL RESEARCH, Basel (CH)

( * ) Notice: Subject to any disclaimer, the term of this patent is extended or adjusted under 35 U.S.C. 154(b) by 15 days.

(21) Appl. No.: 15/760,207

(22) PCT Filed: Sep. 13, 2016

(86) PCT No.: PCT/EP2016/071558
§ 371 (c)(1),
(2) Date: Mar. 14, 2018

(87) PCT Pub. No.: WO2017/046084
PCT Pub. Date: Mar. 23, 2017

(65) Prior Publication Data
US 2018/0256753 A1  Sep. 13, 2018

(30) Foreign Application Priority Data
Sep. 15, 2015  (EP) .................................... 15185327

(51) Int. Cl.
| | | |
|---|---|---|
| A61K 48/00 | (2006.01) | |
| C07K 14/705 | (2006.01) | |
| A61F 9/00 | (2006.01) | |
| A61K 9/00 | (2006.01) | |
| C12N 15/85 | (2006.01) | |
| A61K 38/00 | (2006.01) | |

(52) U.S. Cl.
CPC ........ *A61K 48/0075* (2013.01); *A61F 9/0017* (2013.01); *A61K 9/0048* (2013.01); *A61K 48/005* (2013.01); *C07K 14/705* (2013.01); *C12N 15/85* (2013.01); *A61K 38/00* (2013.01); *C12N 2750/14143* (2013.01); *C12N 2830/008* (2013.01)

(58) Field of Classification Search
CPC .................................................. A61K 48/0075
See application file for complete search history.

(56) References Cited

U.S. PATENT DOCUMENTS

| | | | |
|---|---|---|---|
| 9,579,399 B2 | 2/2017 | Roska et al. | |
| 9,844,579 B2 | 12/2017 | Balya et al. | |
| 9,999,685 B2 | 6/2018 | Roska et al. | |
| 10,179,917 B2 | 1/2019 | Roska et al. | |
| 2009/0088399 A1 | 4/2009 | Balya et al. | |
| 2012/0258530 A1 | 10/2012 | Balya et al. | |
| 2013/0059374 A1 | 3/2013 | Balya et al. | |
| 2015/0344907 A1 | 12/2015 | Roska et al. | |
| 2016/0250282 A1 | 9/2016 | Balya et al. | |
| 2017/0022520 A1 | 1/2017 | Roska et al. | |
| 2017/0119905 A1 | 5/2017 | Roska et al. | |
| 2018/0125925 A1 | 5/2018 | Balya et al. | |
| 2018/0127778 A1 | 5/2018 | Roska et al. | |
| 2018/0298378 A1 | 10/2018 | Jeuttner et al. | |
| 2018/0346529 A1 | 12/2018 | Hartl et al. | |
| 2018/0353617 A1 | 12/2018 | Hartl et al. | |
| 2018/0355354 A1 | 12/2018 | Dalkara et al. | |
| 2018/0355377 A1 | 12/2018 | Hartl et al. | |
| 2019/0054191 A1 | 2/2019 | Hartl et al. | |
| 2019/0209708 A1 | 7/2019 | Roska et al. | |
| 2019/0276847 A1 | 9/2019 | Hartl et al. | |
| 2019/0376082 A1 | 12/2019 | Jeuttner et al. | |
| 2019/0376083 A1 | 12/2019 | Jeuttner et al. | |

FOREIGN PATENT DOCUMENTS

| | | | | |
|---|---|---|---|---|
| JP | WO2001/88188 | * 11/2001 | ............... | C12Q 1/68 |
| WO | 2008/022772 A1 | 2/2008 | | |
| WO | 2009127705 A1 | 10/2009 | | |
| WO | WO2009/127705 | * 10/2009 | ............. | A61K 48/00 |
| WO | 2012/087983 A1 | 6/2012 | | |
| WO | 2013/068413 A1 | 5/2013 | | |
| WO | 2014/033095 A1 | 3/2014 | | |
| WO | 2014/199299 A1 | 12/2014 | | |
| WO | 2015/118507 A1 | 8/2015 | | |
| WO | 2015/121793 A1 | 8/2015 | | |
| WO | 2015128624 A1 | 9/2015 | | |
| WO | 2016/174624 A1 | 11/2016 | | |

(Continued)

OTHER PUBLICATIONS

Alignment of Ishikawa(WO2001/88188) SEQ ID No. 822 with SEQ ID No. 1 (U.S. Appl. No. 15/760,207) (Year: 2019).*
Alignment of SEQ ID No. 6 (STIC search) (Year: 2020).*
Bi, A., et al., "Ectopic expression of a microbial-type rhodopsin restores visual responses in mice with photoreceptor degeneration", Neuron, 50(1): 23-33 (2006).
International Search Report and Written Opinion from PCT/EP2016/071558 dated Dec. 12, 2016.

*Primary Examiner* — Scott Long
(74) *Attorney, Agent, or Firm* — Joshua J. Buchman

(57) ABSTRACT

The present invention relates to an isolated nucleic acid molecule comprising a nucleotide sequence coding for a depolarizing light-gated ion channel functionally linked to a promoter leading to the specific expression of said depolarizing light-gated ion channel in a retinal photoreceptor, or the nucleotide sequence complementary to said nucleotide sequence, for use in treating or ameliorating blindness. The present invention also relates to methods of using such nucleic acid molecules in the treatment of blindness.

25 Claims, 1 Drawing Sheet
Specification includes a Sequence Listing.

(56) References Cited

FOREIGN PATENT DOCUMENTS

| | | |
|---|---|---|
| WO | 2017/046084 A1 | 3/2017 |
| WO | 2017/064642 A1 | 4/2017 |
| WO | 2017/093566 A1 | 6/2017 |
| WO | 2017/093931 A1 | 6/2017 |
| WO | 2017/093934 A1 | 6/2017 |
| WO | 2017/093935 A1 | 6/2017 |
| WO | 2017/093936 A1 | 6/2017 |
| WO | 2017/199156 A1 | 11/2017 |
| WO | 2018/083607 A1 | 5/2018 |
| WO | 2018/099974 A1 | 6/2018 |
| WO | 2018/099975 A1 | 6/2018 |
| WO | 2018/146588 A1 | 8/2018 |
| WO | 2019/097454 A1 | 5/2019 |
| WO | 2019/106027 A1 | 6/2019 |
| WO | 2019/106035 A1 | 6/2019 |
| WO | 2020/084537 A1 | 4/2020 |
| WO | 2020/084538 A1 | 4/2020 |
| WO | 2020/084539 A1 | 4/2020 |
| WO | 2020/084540 A1 | 4/2020 |
| WO | 2020/084541 A1 | 4/2020 |
| WO | 2020/084542 A1 | 4/2020 |

\* cited by examiner

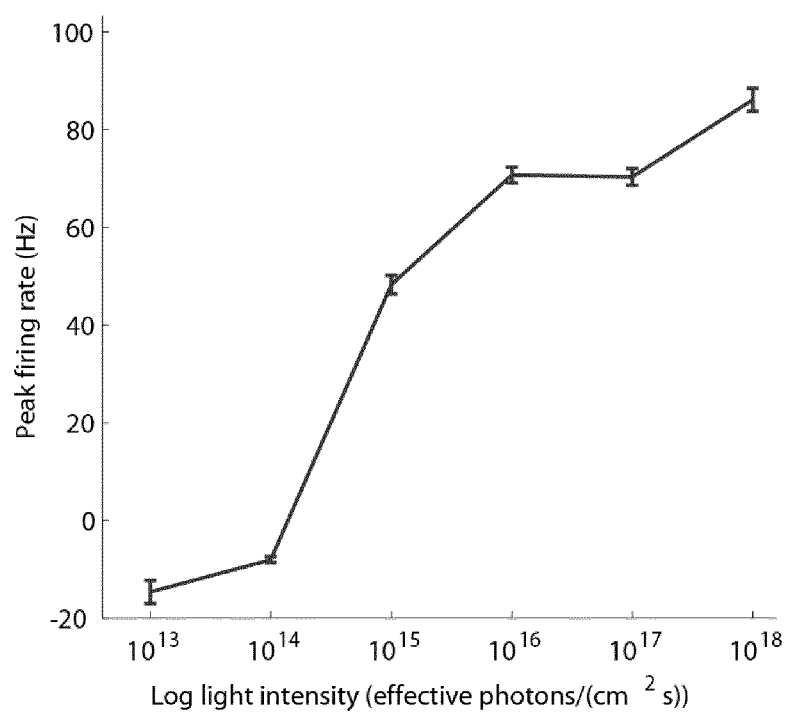

THERAPEUTICAL TOOLS AND METHODS FOR TREATING BLINDNESS BY TARGETING PHOTORECEPTORS

CROSS REFERENCE TO RELATED APPLICATIONS

This application is a U.S. National Phase Application under 35 U.S.C. § 371 of International Application PCT/EP2016/071558, filed on Sep. 13, 2016, which claims priority to EP Application No. 15185327.2, filed on Sep. 15, 2015, the contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 30, 2016, is named 57077_ST25 SQL.txt and is 12,288 bytes in size. No new matter has been added.

FIELD OF THE INVENTION

The present invention relates to methods of treating blindness. The present invention also relates to constructs for use in treating blindness, as well as their use in the manufacture of a medicament for treating blindness.

BACKGROUND OF THE INVENTION

Blindness is a major health problem that disables millions of people worldwide. One of the most common cause of blindness is the disfunction of the retina. The three most common forms of retinal blindness are retinitis pigmentosa (RP), macular denereration (MD) and glaucoma (G). In RP and MD the primary problem is the degeneration of photoreceptors and the consequent loss of photosensitivity. There is thus a need to be able to obviate the problems associated with such degeneration of photoreceptors.

One approach has been to develop a retinal prosthesis, a "seeing eye" chip with as many as 1,000 tiny electrodes to be implanted in the eye. This would have the potential to help people who have lost their sight to regain enough vision to function independently, but the numbers of electrodes is simply insufficient to provide a high degree or level of sight to be obtained. Moreover, there are problems associated with inserting foreign bodies into the eye. Recently a number of genes has been isolated and/or manipulated that when expressed can make cells light sensitive. In some cases additional non-genetic factors are also needed to make cells light sensitive.

One proposal by Eli in 2001 was to use the chlorophyll-containing proteins in spinach to treat vision loss. These proteins give off a small electrical voltage after capturing the energy of incoming photons of light. Although, the research has shown that photosystem I reaction centres can be incorporated into a liposome and are shown to be functional, in that it produces the experimental equivalent of a voltage when light is shone on it, hitherto this has not been shown to work in a retinal cell.

Other work by neurobiologist Richard Kramer at UC Berkeley has looked at re-engineering a potassium channel to be responsive to light rather than voltage, in order to allow insertion of a light activated switch into brain cells normally insensitive to light. However, the channel has to be mutated so that it always stays open and a chemical "plug", attached to the channel, which is sensitive to light such that when lit with long-wavelength UV light, the plug is released from the channel, letting potassium out of the channel. Light of a longer wavelength causes the plug to insert back into the channel and stop release of potassium. It will be appreciated however, that such a system is extremely complex and problems are likely to arise if the channel is delivered to the wrong type of retinal cells.

Bi et al., (Neuron, 50, 2006, p 23-33) discloses the use of microbial-type rhodopsin to restore visual responses in mice with photoreceptor degeneration. However, the expression of the rhodopsin gene is likely to have occurred in a variety of types of cell in the eye which is potentially undesirable and/or problematic. It also appears that the threshold light intensity required for producing responses is much higher than for normal rod and cone photoreceptors, but there is no teaching of how this may be addressed in, for example, low light environments.

An alternative method has been described by some of the present inventors in WO-A-2008/022772, wherein e.g. channelrhodopsin-2 is targeted to e.g. ON-cells. This method has however the disadvantage of being sub-optimal with OFF-cells.

SUMMARY OF THE INVENTION

During further investigations, the present inventors came to realize that the expression of depolarizing light-sensitive molecules in retinal photoreceptors can be extremely useful for e.g. vision restoration. Although it is counterintuitive to express depolarizing light-sensitive molecules in retinal photoreceptors, which normally require hyperpolarization to be activated, the present inventors found that this expression is surprisingly useful and not only works surprisingly well, but could also allow to tune the overall retinal response during vision restoration methods using e.g. the expression of exogenous light-sensitive molecules in discrete retinal cells. In addition, the inventors also found that in disease states, the polarization of the retinal photoreceptors does not always reflect the normal state and can in some cases even be inverted as compared to healthy retinal photoreceptors.

The present invention thus encompasses an isolated nucleic acid molecule comprising a nucleotide sequence coding for a depolarizing light-gated ion channel functionally linked to a promoter leading to the specific expression of said depolarizing light-gated ion channel in a retinal photoreceptor, or the nucleotide sequence complementary to said nucleotide sequence, for use in treating or ameliorating blindness. The depolarizing light-gated ion channel can be a channel rhodopsin, for instance channelrhodopsin-2 or a variant thereof.

The isolated nucleic acid molecule of the invention can have a promoter leading to the expression of said depolarizing light-gated ion channel in retinal photoreceptor selected from the group of human rhodopsin promoter, the human red opsin promoter, the red cone opsin promoter, the arr3 promoter (mCAR), the Grm6 promoter, Fabp7(trunc) (SEQ ID NO:1), Gnat2_500 (SEQ ID NO:2), Gnat2_2kb (SEQ ID NO:3), Arr3_2kb (SEQ ID NO:4), TF_ZFHX3 (SEQ ID NO:5) and TF_GSH2 (SEQ ID NO:6).

In the present invention, the retinal photoreceptor cell can be a rod and/or a cone.

The present invention also encompasses an isolated nucleic acid molecule comprising, or consisting of, the nucleic acid sequence of SEQ ID NO:1, 2, 3, 4, 5 or 6, or consisting of a nucleic acid sequence of at least 200 bp having at least 90% identity to said sequence of SEQ ID NO:1, 2, 3, 4, 5 or 6, respectively, wherein said isolated nucleic acid molecule specifically leads to the expression of a gene in a retinal photoreceptor when a nucleic acid sequence coding for said gene is operatively linked to said isolated nucleic acid molecule.

The present invention further encompasses a recombinant vector comprising the above nucleic acid of the invention.

The present invention also encompasses a host cell comprising the vector of the invention.

The present invention further encompasses a kit comprising an isolated nucleic, a recombinant vector or a host cell of the invention.

The present invention also encompasses a method of treating blindness characterized in that an isolated, a recombinant vector, or a cell of the invention is administered to a patient in need thereof. In said method for treating blindness the administration can be performed through sub-retinal injection.

DESCRIPTION OF THE FIGURE

FIG. 1: CatCh induces ON responses. Full field, white light multi-electrode array RGC recordings. Light intensity expressed in effective photons per $cm^2$ per second. n=263 neurons.

DETAILED DESCRIPTION OF THE INVENTION

The present inventors came to realize that the expression of depolarizing light-sensitive molecules in retinal photoreceptors can be extremely useful for e.g. vision restoration. Although it is counterintuitive to express depolarizing light-sensitive molecules in retinal photoreceptors, which normally require hyperpolarization to be activated, the present inventors found that this expression is surprisingly useful and not only works surprisingly well, but could also allow to tune the overall retinal response during vision restoration methods using e.g. the expression of exogenous light-sensitive molecules in discrete retinal cells. In addition, the inventors also found that in disease states, the polarization of the retinal photoreceptors does not always reflect the normal state and can in some cases even be inverted as compared to healthy retinal photoreceptors.

The present invention thus encompasses an isolated nucleic acid molecule comprising a nucleotide sequence coding for a depolarizing light-gated ion channel functionally linked to a promoter leading to the specific expression of said depolarizing light-gated ion channel in a retinal photoreceptor, or the nucleotide sequence complementary to said nucleotide sequence, for use in treating or ameliorating blindness. The depolarizing light-gated ion channel can be a channel rhodopsin, for instance channelrhodopsin-2 or a variant thereof.

The isolated nucleic acid molecule of the invention can have a promoter leading to the expression of said depolarizing light-gated ion channel in retinal photoreceptor selected from the group of human rhodopsin promoter, the human red opsin promoter, the red cone opsin promoter, the arr3 promoter (mCAR), the Grm6 promoter, Fabp7(trunc) (SEQ ID NO:1), Gnat2_500 (SEQ ID NO:2), Gnat2_2kb (SEQ ID NO:3), Arr3_2kb (SEQ ID NO:4), TF_ZFHX3 (SEQ ID NO:5) and TF_GSH2 (SEQ ID NO:6).

In the present invention, the retinal photoreceptor cell can be a rod and/or a cone.

The present invention also encompasses an isolated nucleic acid molecule comprising, or consisting of, the nucleic acid sequence of SEQ ID NO:1, 2, 3, 4, 5 or 6, or consisting of a nucleic acid sequence of at least 200 bp having at least 90% identity to said sequence of SEQ ID NO:1, 2, 3, 4, 5 or 6, respectively, wherein said isolated nucleic acid molecule specifically leads to the expression of a gene in a retinal photoreceptor when a nucleic acid sequence coding for said gene is operatively linked to said isolated nucleic acid molecule.

The present invention further encompasses a recombinant vector comprising the above nucleic acid of the invention.

The present invention also encompasses a host cell comprising the vector of the invention.

The present invention further encompasses a kit comprising an isolated nucleic, a recombinant vector or a host cell of the invention.

The present invention also encompasses a method of treating blindness characterized in that an isolated, a recombinant vector, or a cell of the invention is administered to a patient in need thereof. In said method for treating blindness the administration can be performed through sub-retinal injection.

Compositions comprising the nucleic acid molecules of the invention are also encompassed by the present invention. Said compositions can be pharmaceutically acceptable compositions.

"Retinal photoreceptors" comprise rods and cones. The retina can be viewed as a parallel image processor that acquires images via a mosaic of photoreceptors and that extracts various visual features from the acquired images. Rod photoreceptors respond directly to light at lower intensities and cone photoreceptors at higher intensities. The cellular infrastructure that underlies parallel processing consists of mosaics of local neuronal circuits. The retina has ~20 such circuit mosaics, built from more than 60 cell types, which independently extract different features from the visual world. Each mosaic has an associated mosaic of output cells, the ganglion cells, which relay the computed feature to higher brain centers. Each cone in the retina is connected to around 10 types of cone bipolar cells, and each of these bipolar cells is connected to several types of ganglion cells. Cones, bipolar cells, and ganglion cells use the excitatory neurotransmitter glutamate to communicate. Communication between cones and bipolar cells is modified by the inhibitory horizontal cells, and communication between bipolar cells and ganglion cells is modified by a large variety of inhibitory amacrine cells. Cones respond to light by lowering their membrane voltage; i.e., they hyperpolarize. Half of the cone bipolar cells also hyperpolarize (OFF cells), whereas the other half increase their membrane voltage, depolarizing when light intensity increases (ON cells). The polarity of the ganglion cell responses is determined by the polarity of the bipolar cells from which they receive input. Each rod is connected to a special bipolar cell type called the rod bipolar cell. Rod bipolar cells "talk" to the so-called AII amacrine cells, which then provide excitatory input to the axon terminals of ON cone bipolar cells and inhibitory input to OFF cone bipolar cell terminals. Rods (photoreceptors) are hyperpolarized by light, whereas rod bipolar cells and AII amacrine cells are depolarized: These are therefore ON cells. Retinal cells are arranged in mosaics, covering the entire retina. The only exception to the mosaic arrangement is a special area of the retina in some primates and in a few predatory birds and reptiles. This area is called the fovea and is the place with the highest cone density. The human fovea, also called macula, has no rods within its center, and the only cellular compartment that is organized in a mosaic fashion is the cone outer segment. Foveal cone cell bodies are piled on top of each other, whereas cell bodies of all other cell types are shuffled to the side, forming a concentric ring of cell bodies.

By "blindness" is meant total or partial loss of vision. Typically the medicament may be used to treat blindness associated with macular degeneration, glaucoma and/or retinitis pigmentosa. However, it is to be appreciated that any disease or condition which leads to degeneration or non-functioning of photoreceptors in the eye may be treated using the medicament. Moreover, without wishing to be bound by theory, it is believed that the present invention will be particularly effective for curing blindness at early stages of retinal degeneration (rd) when photoreceptor function is lost but the photoreceptor-to-bipolar synapse may still be intact.

An "active fragment of a depolarizing light-gated ion channel" is a fragment which when expressed generates a polypeptide which is still capable of functioning as a light capturing molecule which causes a subsequent flow of ions out of the cell in which the channel is located and a consequent change in voltage.

By "hyperpolarisation" is meant the decrease of the membrane potential of a cell (made more negative). By "depolarisation" is meant the increase of the membrane potential of a cell (made more positive).

It will be appreciated that the present invention also extends to methods of treating therapeutically blindness by administering to a patient suffering blindness, a DNA construct according to the invention comprising a depolarizing light-gated ion channel gene sequence or active fragment thereof, which gene sequence or fragment thereof is capable of expressing one or more copies of the depolarizing light-gated ion channel protein in a retinal cell, whereby expression of said one or more copies of the depolarizing light-gated ion channel protein render the cell photosensitive so as to enable treatment or amelioration of blindness.

Typically, the depolarizing light-gated ion channel gene sequence of the invention or fragment thereof may be administered to a subject in the form of a recombinant molecule comprising said light-gated ion channel gene sequence or active fragment under appropriate transcriptional/translational controls to allow expression of said depolarizing light-gated ion channel protein when administered to retinal cells of a subject. It will be appreciated that the depolarizing light-gated ion channel sequence or fragment may be under control of a suitable promoter, such as a constitutive and/or controllable promoter.

The present invention also therefore provides a recombinant molecule of the invention comprising a depolarizing light-gated ion channel gene sequence or active fragment thereof for use in therapy. The recombinant molecule may be in the form of a plasmid, phagemid or viral vector. Furthermore, recombinantly expressed, or chemically synthesized depolarizing light-gated ion channel protein, or functionally important fragments thereof, may be produced and applied to the eye via a suitable ointment or other pharmaceutical vehicle, as a treatment or prophylactic measure for treating said aforementioned diseases.

Many different viral and non-viral vectors and methods of their delivery, for use in gene therapy, are known, such as adenovirus vectors, adeno-associated virus vectors, retrovirus vectors, lentiviral vectors, herpes virus vectors, liposomes, naked DNA administration and the like. A detailed review of possible techniques for transforming genes into desired cells of the eye is taught by Wright (Br J Ophthalmol, 1997; 81: 620-622). Moreover, it may also be possible to use encapsulated cell technology as developed by Neurotech, for example.

The light-gated ion channel gene can be a rhodopsin gene, such as a rhodopsin from a microorganism, such as a unicellular alga, typically from the species Chlamydononas, especially Chlamydomonas reinhardtii. A preferred rhodopsin is Channelrhodopsin-2 (ChR2) which is a light gated cation channel from C. reinhardtii, see for example, Boyden et al 2005 (Nature Neuroscience, 8, 9; 1263-1268) and WO-A-2003/084994. Variants of Channelrhodopsin-2 are also very suitable for the present invention. An example of such y variant is CatCh, a L132C mutant of ChR2 (Nat Neurosci. 2011 April; 14(4):513-8. doi: 10.1038/nn.2776. Ultra light-sensitive and fast neuronal activation with the $Ca^{2+}$-permeable channelrhodopsin CatCh. Kleinlogel S1, Feldbauer K, Dempski R E, Fotis H, Wood P G, Bamann C, Bamberg E.).

The retinal photoreceptors to which the medicament or vector are to be administered might have lost their photosensitivity but are usually not "dead" and can be used to express the depolarizing light-gated ion channel gene. Moreover expression of the depolarizing light-gated ion channel gene in photoreceptors may prevent or show down degeneration.

It is understood that it is preferable that expression of the light-gated ion channel gene of the invention is controlled by way of a cell specific promoter. Thus a cell specific promoter may be used to ensure that the light-gated ion channel gene is only expressed in a specific cell type.

Once expressed in an appropriate retinal cell, the depolarizing light-gated ion channel protein inserts within the plasma membrane of the cell, rendering the cell photosensitive and able to cause ion transport, cation or anion, in response to light. Nevertheless, although it is known that the retina is sensitive to very wide ranges of light intensities due to the adaptive nature of photoreceptors, light-gated ion channels or pumps may not be able to adapt and may therefore respond only to a narrow range of light intensities. If this is the case, such a limitation may be mitigated by use of image intensifiers and/or image converters known in the art. For example, a patient who has been treated by the above described method, may wear, image intensifiers/enhancers mounted, for example, on spectacles or the like.

By way of an example, an image intensifying device, such as those provided by Telesensory (http://www.telesensory.com), may be combined with a retinal scanning device (RSD) as developed by Microvision (http://www.microvision.com/milprod.html), to provide a head-worn apparatus capable of delivering a bright, intensified image directly to the retina of a patient with impaired vision (http://www.telesensory.com/home8.html). Briefly, a RSD projects images onto the retina such that an individual can view a large, full-motion image without the need for additional screens or monitors. Thus, by projecting an intensified image directly to the retina of an individual with impaired vision, it may be possible to improve vision in those considered to be blind.

In case of expressing the depolarizing light-gated ion channel in retinal bipolar or ganglion cells some aspects of the network processing capabilities of the retina can be lost. For example horizontal cell mediated lateral inhibition can be lost if light activates bipolar or ganglion cells. In these cases a retina like processor (D. Balya and B. Roska: "Retina model with real time implementation", International Symposium on Circuits and Systems ISCAS 2005, Kobe, Japan, May, pp. 5222-5225, also see http://www.anafocus.com/ and http://www.eutecus.com/) can be combined with the Microvision system.

These and other aspects of the present invention should be apparent to those skilled in the art, from the teachings herein.

For convenience, the meaning of certain terms and phrases employed in the specification, examples, and appended claims are also provided below.

The singular forms "a," "an," and "the" include plural reference unless the context clearly dictates otherwise.

"Halorhodopsin" is a light-driven ion pump, specific for chloride ions, and found in phylogenetically ancient "bacteria" (archaea), known as halobacteria. It is a seven-trans-membrane protein of the retinylidene protein family, homologous to the light-driven proton pump bacteriorhodopsin, and similar in tertiary structure (but not primary sequence structure) to vertebrate rhodopsins, the pigments that sense light in the retina. Halorhodopsin also shares sequence similarity to channelrhodopsin, a light-driven ion channel. Halorhodopsin contains the essential light-isomerizable vitamin A derivative all-trans-retinal. Halorhodopsin is one of the few membrane proteins whose crystal structure is known. Halorhodopsin isoforms can be found in multiple species of halobacteria, including *H. salinarum*, and *N. pharaonis* (NphR). Much ongoing research is exploring these differences, and using them to parse apart the photocycle and pump properties. After bacteriorhodopsin, halorhodopsin may be the best type I (microbial) opsin studied. Peak absorbance of the halorhodopsin retinal complex is about 570 nm. Recently, halorhodopsin has become a tool in optogenetics. Just as the blue-light activated ion channel channelrhodopsin-2 opens up the ability to activate excitable cells (such as neurons, muscle cells, pancreatic cells, and immune cells) with brief pulses of blue light, halorhodopsin opens up the ability to silence excitable cells with brief pulses of yellow light. Thus halorhodopsin and channelrhodopsin together enable multiple-color optical activation, silencing, and desynchronization of neural activity, creating a powerful neuroengineering toolbox. Further variants of halorhodopsin have been developped, e.g. enhanced NphR (eNphR). For the purpose of the present invention, said variants are also included in the definition of "Halorhodopsin".

"Polynucleotide" and "nucleic acid", used interchangeably herein, refer to polymeric forms of nucleotides of any length, either ribonucleotides or deoxyribonucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

These terms further include, but are not limited to, mRNA or cDNA that comprise intronic sequences. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids, PNA and LNA. Polynucleotides may further comprise genomic DNA, cDNA, or DNA-RNA hybrids.

"Sequence Identity" refers to a degree of similarity or complementarity. There may be partial identity or complete identity. A partially complementary sequence is one that at least partially inhibits an identical sequence from hybridizing to a target polynucleotide; it is referred to using the functional term "substantially identical". The inhibition of hybridization of the completely complementary sequence to the target sequence may be examined using a hybridization assay (Southern or Northern blot, solution hybridization and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarities (e.g., less than about 30% identity); in the absence of non-specific binding, the probe will not hybridize to the second non-complementary target sequence.

Another way of viewing sequence identity in the context to two nucleic acid or polypeptide sequences includes reference to residues in the two sequences that are the same when aligned for maximum correspondence over a specified region. As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Gene" refers to a polynucleotide sequence that comprises control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

"Expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein.

"Cell type" refers to a cell from a given source (e.g., tissue or organ) or a cell in a given state of differentiation, or a cell associated with a given pathology or genetic makeup.

"Polypeptide" and "protein", used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

A "fragment of a protein" refers to a protein that is a portion of another protein. For example, fragments of proteins may comprise polypeptides obtained by digesting full-length protein isolated from cultured cells. In one embodiment, a protein fragment comprises at least about 6 amino acids. In another embodiment, the fragment comprises at least about 10 amino acids. In yet another embodiment, the protein fragment comprises at least about 16 amino acids.

An "expression product" or "gene product" is a biomolecule, such as a protein or mRNA, that is produced when a gene in an organism is transcribed or translated or post-translationally modified.

"Host cell" refers to a microorganism, a prokaryotic cell, a eukaryotic cell or cell line cultured as a unicellular entity that may be, or has been, used as a recipient for a recombinant vector or other transfer of polynucleotides, and includes the progeny of the original cell that has been transfected. The progeny of a single cell may not necessarily be completely identical in morphology or in genomic or total DNA complement as the original parent due to natural, accidental, or deliberate mutation.

The term "functional equivalent" is intended to include the "fragments", "mutants", "derivatives", "alleles", "hybrids", "variants", "analogs", or "chemical derivatives" of the native gene or virus.

"Isolated" refers to a polynucleotide, a polypeptide, an immunoglobulin, a virus or a host cell that is in an environment different from that in which the polynucleotide, the polypeptide, the immunoglobulin, the virus or the host cell naturally occurs.

"Substantially purified" refers to a compound that is removed from its natural environment and is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% or more free from other components with which it is naturally associated.

"Diagnosis" and "diagnosing" generally includes a determination of a subject's susceptibility to a disease or disorder, a determination as to whether a subject is presently affected by a disease or disorder, a prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

"Biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived therefrom and the progeny thereof. The term specifically encompasses a clinical sample, and further includes cells in cell culture, cell supernatants, cell lysates, serum, plasma, urine, amniotic fluid, biological fluids, and tissue samples. The term also encompasses samples that have been manipulated in any way after procurement, such as treatment with reagents, solubilization, or enrichment for certain components.

"Individual", "subject", "host" and "patient", used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Hybridization" refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency.

"Stringent conditions" refers to conditions under which a probe may hybridize to its target polynucleotide sequence, but to no other sequences. Stringent conditions are sequence-dependent (e. g., longer sequences hybridize specifically at higher temperatures). Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the target sequence hybridize to the target sequence at equilibrium. Typically, stringent conditions will be those in which the salt concentration is at least about 0.01 to about 1.0 M sodium ion concentration (or other salts) at about pH 7.0 to about pH 8.3 and the temperature is at least about 30° C. for short probes (e. g., 10 to 50 nucleotides). Stringent conditions may also be achieved with the addition of destabilizing agents, such as formamide.

"Biomolecule" includes polynucleotides and polypeptides.

"Biological activity" refers to the biological behavior and effects of a protein or peptide. The biological activity of a protein may be affected at the cellular level and the molecular level. For example, the biological activity of a protein may be affected by changes at the molecular level. For example, an antisense oligonucleotide may prevent translation of a particular mRNA, thereby inhibiting the biological activity of the protein encoded by the mRNA. In addition, an immunoglobulin may bind to a particular protein and inhibit that protein's biological activity.

"Oligonucleotide" refers to a polynucleotide sequence comprising, for example, from about 10 nucleotides (nt) to about 1000 nt. Oligonucleotides for use in the invention are for instance from about 15 nt to about 150 nt, for instance from about 150 nt to about 1000 nt in length. The oligonucleotide may be a naturally occurring oligonucleotide or a synthetic oligonucleotide.

"Modified oligonucleotide" and "Modified polynucleotide" refer to oligonucleotides or polynucleotides with one or more chemical modifications at the molecular level of the natural molecular structures of all or any of the bases, sugar moieties, internucleoside phosphate linkages, as well as to molecules having added substitutions or a combination of modifications at these sites. The internucleoside phosphate linkages may be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5' linkages, and combinations of such similar linkages. The phosphodiester linkage may be replaced with a substitute linkage, such as phosphorothioate, methylamino, methylphosphonate, phosphoramidate, and guanidine, and the ribose subunit of the polynucleotides may also be substituted (e. g., hexose phosphodiester; peptide nucleic acids). The modifications may be internal (single or repeated) or at the end (s) of the oligonucleotide molecule, and may include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e. g., 3'-substituted ribonucleotides or deoxyribonucleotide monomers), any of which are bound together via 5' to 3' linkages.

"Biomolecular sequence" or "sequence" refers to all or a portion of a polynucleotide or polypeptide sequence.

The term "detectable" refers to a polynucleotide expression pattern which is detectable via the standard techniques of polymerase chain reaction (PCR), reverse transcriptase-(RT) PCR, differential display, and Northern analyses, which are well known to those of skill in the art. Similarly, polypeptide expression patterns may be "detected" via standard techniques including immunoassays such as Western blots.

A "target gene" refers to a polynucleotide, often derived from a biological sample, to which an oligonucleotide probe is designed to specifically hybridize. It is either the presence or absence of the target polynucleotide that is to be detected, or the amount of the target polynucleotide that is to be quantified. The target polynucleotide has a sequence that is complementary to the polynucleotide sequence of the corresponding probe directed to the target. The target polynucleotide may also refer to the specific subsequence of a larger polynucleotide to which the probe is directed or to the overall sequence (e.g., gene or mRNA) whose expression level it is desired to detect.

A "target protein" refers to a polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid may also refer to the specific substructure of a larger protein to which the protein-capture agent is directed or to the overall structure (e. g., gene or mRNA) whose expression level it is desired to detect.

"Complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

"BLAST" refers to Basic Local Alignment Search Tool, a technique for detecting ungapped sub-sequences that match a given query sequence.

"BLASTP" is a BLAST program that compares an amino acid query sequence against a protein sequence database. "BLASTX" is a BLAST program that compares the six-frame conceptual translation products of a nucleotide query sequence (both strands) against a protein sequence database.

A "cds" is used in a GenBank DNA sequence entry to refer to the coding sequence. A coding sequence is a sub-sequence of a DNA sequence that is surmised to encode a gene.

A "consensus" or "contig sequence", as understood herein, is a group of assembled overlapping sequences, particularly between sequences in one or more of the databases of the invention.

The nucleic acid molecules of the present invention can be produced by a virus harbouring a nucleic acid that encodes the relevant gene sequence. The virus may comprise elements capable of controlling and/or enhancing expression of the nucleic acid. The virus may be a recombinant virus. The recombinant virus may also include other functional elements. For instance, recombinant viruses can be designed such that the viruses will autonomously replicate in the target cell. In this case, elements that induce nucleic acid replication may be required in a recombinant virus. The recombinant virus may also comprise a promoter or regulator or enhancer to control expression of the nucleic acid as required. Tissue specific promoter/enhancer elements may be used to regulate expression of the nucleic acid in specific cell types. The promoter may be constitutive or inducible.

A "promoters" is a region of DNA that is generally located upstream (towards the 5' region) of the gene that is needed to be transcribed. The promoter permits the proper activation or repression of the gene which it controls. In the context of the present invention, the promoters lead to the specific expression of the light-gated ion channels in photoreceptors. "Specific expression" means that at least more than 75% of the cells expressing the gene of interest are of the type specified, i.e. photoreceptors in the present case. Examples of promoters which are suitable for the expression of constructs in retinal photoreceptors are the human rhodopsin promoter (Allocca et al., Novel AAV serotypes efficiently transduce murine photoreceptors, J Virol. (2007)), the human red opsin promoter (Nathan et al., Science. 1986 Apr. 11; 232(4747):193-202), the GRM6 promoter, the red cone opsin promoter, or the arr3 promoter (mCAR) (Zhu, X. et al. Mouse cone arrestin gene characterization: promoter targets expression to cone photoreceptors. FEBS Letters 524, 116-122 (2002)). In addition, the following promoters have been found to be suitable for the specific and almost exclusive (more than 75%) expression of genes in retinal photoreceptors and to be also extremely well suited for the present invention:

```
Fabp7(trunc) (SEQ ID NO: 1:
AGCTAGCACAGCACTAGGCTAAAGCGTACTGAGCCCTTGTCTTCCGTGGG

AGCTGCAGAGTGGGATGCATGCGTTGTGAGCTGAGGCTCAAGCTGCGCTG

GCAGAAGAGCAGGGGTTGCCTTGTCAGACTCCAGGGTCTCTTTCTCTCTG

AGCCTGGGAAAGTGCCACTTTATTGGATCTATAAAGCCGGGGGGGGGGG

GGGGGAGGAATCTCAAGGTGAAGAGGAAGTTCACAGACCCCTCTAACGCC

TCTATTAGAACCTTCCAGCTATTCTCTCATACTTGTACACTGAGCTGGCA

CACAGTATAGGCAAGTTCTATTCGCATCACCCCTCTAGTTCCTGTCTCCC

TGGTTATGCAAGCCTCATATTTAGGTAGATGTGACCTTAGGAAACCAAAA

TATCCTTTAAGATCTTACTAACTGGTTGCCTGTTCAGCTTTTCCACATTG

ATCCTGTAGCCCCCTCGAGGAGGTGAAGGAAAAAAATCTCCTCTTTGTTT

CTCTAACTCATTAATGAATTTTAAGGGCACTCTGTAAGGTTCCTTTCCCA

TTCTGGTCTGGTTCGTACATTCTGAGAAACACACTGTGTTGTGTTGAGAG

TTGGCTCCCTAGCTACACTGTCTGTCACATTGATGCTCTGAGTAGGGACA

GGGTTCATCTAGGAAATATATTTTCACTCACACTCTGTATCTTTTCCTAG

TTTGGCATATTCTAGTCTGCATTTGGCTCTCTGTTTAAATATAAAAGAAA

ACTAAAACACACCCTTCAGACGCCTATGTCTGAAAAATCTGGCATTTCCG

TGGGTTTTTCTTTAAGGAGGCCTTCATTTGTAACCAACACCATGCTCTCC

TTAAGGAAATCAATCTCAATGCCCTATTATCCTTCCCTTTTCTTTCCTCC

CAGTTTGAGGCTGCAGTTGCCTTTTTTTTCTTATCCCTGCTGAACCTG

AAAAACCCTCTCTTTTCTACAGTTTTCTGTTCCCAGGCCCCGCTGACTTC

CTTTAGAGCATGGGGGGGGGGGATCAGGATTGTGATGTGTGAACTGGG

AGGATCTTGACCTACTCCGCTAACCCAGTGGCCTGAGCAAATCACAAGGA

GGATTGGAGCCATCTGCCCAGCCCCTCCCCCACGGCAGCCTGCTGGAAAG

AGACAAGTTAGTCATTCAAATGATTGGCTTTTTGCCCGCTTCTTCTCTAA

ATAAGAAGGCAGCAGCTTCTGCTGAGGT),

Gnat2_500 (SEQ ID NO: 2:
CATCCTGAGAGATGAGCCAGGACAAAGAACCAGTAATAGCTCCTGGAGCA

GCACATCTGTTTTGCCAGGATTATCCCTTGGATCTCTTAAAACCGAGACC

TTGTAATCTGAAGACTCAACTTGGGCTGTACCCTTAACCTTCAGCTCTAT

GATGCAAGTGAGTCCACAGGACCGGAGGCTTTGAGATGAGCTTTTCAGAA

GGGAGGAGTTGGCCGCTTGCTCCCAGAGCTCCAGCACCTGCATTCTTCTG

GCTATGTCAGAAGCCAGATCATTTCCCTCGTTAAAAACAAAAACAAAAA

ACAAACAAACAAAATGTTAGTCTTTGCCCTTTATCTGCCTGGCAAAGCTT

TTAATTGGCTTGATCTGTCATTCCGCTAGACATAAAGGGGACAATCCCCG

GATTAGGAAGGAGCTCTCCAGCTCGGGTAAGGAGTCTCAAGGCAAGGTAG

GCAAGCACCACCGGTCCGCACTCTCGCCCAGCTTTTACGGGAAGAAGAG

A),

Gnat2_2kb (SEQ ID NO: 3:
AGAGGCAGGCCGAGTTTGAGGCCAGCCTGGTCTACACAGGCGTTCTAGGA

GAACCTGTCTCATATGCACATGGGCCTGGGATTACACATACAACTGCAAT

GGCAGCACTTGGAAAGCGGAAGCAGGAGAATCGGAATTTCACACTCATCC

TTCATTATAGAAGTCCAAACCTGTGCTAAGCTACTTGGACATCGCTAAAA

AACAGCAAAAATCTTTCTAGGAATTGCCAATGTATACACACCAAGTTGTA

TTTTTGTAGGGCAGACTTTTCCAACTTGCCAGATGATAATAATCATTTAT

ATTAGCTACATTTCAGGCTCCAGAATTAACACTGTTACTGAAATGTATAG

GTTCTAAAACATACCATTTCCAAATATTTTAAAGGATTAACATTTTTGAA

AAGCATGTGATCTTCCAACCATATTTTAGGGAACAGACATAAGAAGTAGG

CAAGTTTGGGAAGAAACAGTTCCTGAGGGCATTTCTTCCCAACCTTGAAT

GCCCTGTGGGTTAACTGAGGTCTTGGTAAAATGTAGATTATTTACTGGAC

TTTTTGAACTGAGAGTGCATTTCTAACAAAACTCCAGGGTATGTGGTCCT

TGCATTACATATGGGGTAGCAACATTCTAAAGCAGTGTTTTTCAACCTGT

GGATCAAGACCCACAGAAGTCACATAGCAGATATCCTGCCTATTAGATAT

TTACATTAAGATTCAGAGCAGTAGCAGAATAGGAGTCATCCCAACCTGAG

GAACTGCATCAGAGTCCCAGCATCAGGAAGGGTGAGAGCCACTGAGCTAA

AGTCCTCTAGGTGAGGGGGCTGCCCCGGAAAGACTCATTTAAATGAAACC

ACTGACACAGAGAGCTGACAGATGAGGTGGGTTCCGTGTCTGTGAGGCTC

TGCTGGTCGTCTCCTCACTCCCATGGAAGAACCACCGAGATGAGGGCGAG

GGGCAGAGCTAACCCAGCCTCTAAGTAGGCAGAGTCTAGTGTCCAGCTGC

CCAAGGAAGAAGTTTGCTGTGTGAGGTGGCCCTGATGTCCGCACACACAA

AATGCCAGTGAAGTCTACTTGACCAAGTGAAGCTGGTGTGGAATGGGAAG

AAGCACACACAGTCAGTCTCTCTGCACACACTCTGTCCTTCACTTCTTCA

CTTACCAGAGATTTGATGAGAACCTACTAGCAGATCAGATTTGATCCCTG

AGTGGAAAAAACGTACAGTGGGAGATAAAAGAGGAAAACAACGGATCTGA

GTTTGAGGTTAGCCTAGTCTGAGCAAGCCGGATACACAGTAAGACCCTGT

CTCACATACATCCACTCGCACGCGCGCGCACACAAACACACACACACA

CACACACACACACACACACACACATCGTGCTAAGGACAAGATAGGC

ATCCTGAGAGATGAGCCAGGACAAAGAACCAGTAATAGCTCCTGGAGCAG
```

-continued

```
CACATCTGTTTTGCCAGGATTATCCCTTGGATCTCTTAAAACCGAGACCT
TGTAATCTGAAGACTCAACTTGGGCTGTACCCTTAACCTTCAGCTCTATG
ATGCAAGTGAGTCCACAGGACCGGAGGCTTTGAGATGAGCTTTTCAGAAG
GGAGGAGTTGGCCGCTTGCTCCCAGAGCTCCAGCACCTGCATTCTTCTGG
CTATGTCAGAAGCCAGATCATTTCCCTCGTTAAAAACAAAAACAAAAAAA
CAAACAAACAAAATGTTAGTCTTTGCCCTTTATCTGCCTGGCAAAGCTTT
TAATTGGCTTGATCTGTCATTCCGCTAGACATAAAGGGGACAATCCCCGG
ATTAGGAAGGAGCTCTCCAGCTCGGGTAAGGAGTCTCAAGGCAAGGTAGG
CAAGCACCACCGGTCCGCACTCTCGCCCAGCTTTTACGGGAAGAAGAGAA
TGTTACTCTATCCTAACATATTTTTCCTTTTCCTCTATCTCACAGATAGG
AAAAATTTAAGAGCCAGAGGGAACGTCCCTTCTCAGAGGAGACAGCAGA
A),
Arr3_2kb (SEQ ID NO: 4:
CTCTCCTCCCATTGATGACTGACTAGGCCATCCTCTGCTACATAGGTGGC
TGGAGCCTGAGTCCCTCCTTGTGTACTCTTTGGTTGGTGGTTTACTCTGG
GGGTACTGGTTAGTTCGTATTGTTGTTCCTCCTAGGGGACTGCAAACCCC
TTCAGCTCCTTGGGTCCTTTCTCTAGTTCTTCTTTGGGGACCCTGTGCTC
AGTTCAATGGATGGCCAATTTCCTTCTTAAATGCCCCTAGCAGTAACTGT
TAGGTCTCAATCCCAAGACAAATGTCTGAGGTGCCTATTTAACAGATCAA
AGCGGACCTGGCCTCAGGTTATCCCAGTCCCTCCCTGTACCTCAGTCCCT
ACCCATCACCAACTCTCCAGCCCAGAGCTTGGGCTGCACTTCCCCCACGG
TTCTTCCCATTTTGGCTACATGGTCTTTTTTTTTACCTTTTTGGTTCCTT
TGGCCTTTTGGCTTTTGGCTTCCAGGGCTTCTGGATCCCCCCCAACCCCT
CCCATACACATACACATGTGCACTCGTGCACTCAACCCAGCACAGGATAA
TGTTCATTCTTGACCTTTCCACATACATCTGGCTATGTTCTCTCTCTTAT
CTACAATAAATCTCCTCCACTATACTTAGGAGCAGTTATGTTCTTCTTCT
TTCTTTCTTTTTTTTTTTTTCATTCAGTAACATCATCAGAATCCCCTAG
CTCTGGCCTACCTCCTCAGTAACAATCAGCTGATCCCTGGCCACTAATCT
GTACTCACTAATCTGTTTTCCAAACTCTTGGCCCCTGAGCTAATTATAGC
AGTGCTTCATGCCACCCACCCCAACCCTATTCTTGTTCTCTGACTCCCAC
TAATCTACACATTCAGAGGATTGTGGATATAAGAGGCTGGGAGGCCAGCT
TAGCAACCAGAGCTGGAGGCTGATGCGAGCTTCATCTCTTCCCTCAGGTA
ATATTCTAAATCTCTCTGCTTCTAGCCCATACTAAGTCCACCTCCTTTGC
CTTTAGCATCTTCTTTAGGAGGAGAGGGGCATCTTTTCTGATGCAAGCAA
TGGATTTTTCAGGCTGATGTAAGAGACTTCTAGAACTCAGCACCCCCCCC
CAACTCATCCCTCTGACCAAGCCTACTATGTTTTGAAGGAAAGCACCAGA
AAGACATTTCCCTCTCTATGCTTCCCTAGCACCTTAAGCGTGGGGACAGG
ATGGAAATGTTTGGGGAAAGTGACAAGAGAGATGATGAGTAAGGGCAAAG
AGGGCTTTCGGCCTCCACAGAGGCTTCTACTGCCACCCCCCAAGAAAGTA
TGAGCGCAACCCTTTCTGTTCTACAGCTTTCCCTCTTCTTTCCCCCACCT
CCCCCCTGTTCTTCCTTCTGAGCTGGAGGTCAAAAGCATCCCAATTCAGG
GTCAAGTCCAGTACAGGGACAAAAAGAAATTTCATCCATTCATTTATTTA
TTCATATAGTTAACTGACTGTGTGCCTGTTGAAGTTCAGTATCAATGCAG
CCCAAGGAACGTATTTAAGAGATGGAGTATGAGCAAGTAGGATAAATAGA
AGGGGTTAAAAAATAAGATGAGGAGCAATCAAGAAAGACACTGGACATTC
CTCTAGCTTTCACACACATGCACCTGTGCATGCATGGATACATGCACAGG
CATTCGCTCATGCACATACACATGAGAGAGAGAGAGAATGAGAGAGAGAG
AGAGAGAGAGAGAGAGAGAGAGAGAGAGAGAGAGAGAGAGAGAGAGAGAG
AAAGAGAGAAAGAGAGAAAGAGAGAAAGAGAATGTAGTGCAATGGTTGGG
TAAGTGTGTAACTGAAGAGTTGCCCTAAGAAGAGGAAAAAAAAAAAGGAA
GCATTGAGTGTTGGTGTGGTATCTCAGGCAGTTAATTTATATTACACTAG
GTGTATCATTATGGAATATTATAGTGCACTAAAAAAAAAAGGATTAAATA
ACTGAGTGTTCCTCTTCCCCTCATCTCAGGAAAGATTCAACTGGCCAG
C),
TF_ZFHX3 (SEQ ID NO: 5:
AGATCTATTAGTAAAATTAACTACACCTGGTCCTTTATGTCATTAACTAC
ACGTCAGTCGTTCTATTATTAACTACACAGAACTTACTATATAATTAACT
ACACCGCGCATTTGGATATATTAACTACACAACTTTGCTTAATAAATTAA
CTACACCCGTAACGGATTCTCATTAACTACACGTTTCATTACGAGGGATT
AACTACACATAGCCCCCGGAGGCATTAACTACACTTTTTGAGGTCGCGAA
TTAACTACACTTCGACTCGCAGGACATTAACTACACTATACCGATAACGC
AATTAACTACACAAATTTTTTATGAAGATTAACTACACTGTTCGCTCCTG
CCTATTAACTACACGAGGCCGTATTTCCAATTAACTACACCCGAGACACA
AGATAATTAACTACACTTAACCAGATGGCAGATTAACTACACGTACGGGC
AGGCCCGATTAACTACACCGGCTGTCATTCCTCATTAACTACACATATCA
CGACTTGTGATTAACTACACGCTCGAGATCTGCGATCTGCATCTCAATTA
GTCAGCAACCATAGTCCCGCCCCTAACTCCGCCCATCCCGCCCCTAACTC
CGCCCAGTTCCGCCCATTCTCCGCCCCATCGCTGACTAATTTTTTTATT
TATGCAGAGGCCGAGGCCGCCTCGGCCTCTGAGCTATTCCAGAAGTAGTG
AGGAGGCTTTTTGGAGGCCTAGGCTTTTGCAAA),
and
TF_GSH2 (SEQ ID NO: 6:
GTACTGCGGACATCCGCTAATTAGCATAACCCGCAAGGATGTAGCTAATT
AGCATATCACGGGAGACTGGGGCTAATTAGCATAAAAAGTCTCCCGCCTG
CTAATTAGCATACGAGACTCTAGAATCGCTAATTAGCATATCAGTCAAAC
CACTTGCTAATTAGCATAAGCATCGCGCTATTTGCTAATTAGCATAAATG
TTACATACATCGCTAATTAGCATATGATAGCACTGTCAAGCTAATTAGCA
TATCAGCCGCACGCATGGCTAATTAGCATACGAATACCACAAGCTGCTAA
TTAGCATACGGTTAAAATAATACGCTAATTAGCATATCAAAGACGACAGA
AGCTAATTAGCATAGATCACCATCACCACGCTAATTAGCATACGTTAATG
CTGTTCTGCTAATTAGCATAGAAATTGTTGATCTGGCTAATTAGCATACC
CGCCTTCCTGAACGCTAATTAGCATACGGTACGTCGAGATTGCTAATTAG
CATATGTACTGAACCCATAGCTAATTAGCATAATAAATTACTAATCCGCT
```

-continued

```
AATTAGCATAGCTCGAGATCTGCGATCTGCATCTCAATTAGTCAGCAACC

ATAGTCCCGCCCCTAACTCCGCCCATCCCGCCCCTAACTCCGCCCAGTTC

CGCCCATTCTCCGCCCCATCGCTGACTAATTTTTTTATTTATGCAGAGG

CCGAGGCCGCCTCGGCCTCTGAGCTATTCCAGAAGTAGTGAGGAGGCTTT

TTTGGAGGCCTAGGCTTTTGCAAA)
```

Contaminant components of its natural environment are materials that would interfere with the methods and compositions of the invention, and may include enzymes, hormones, and other proteinaceous or nonproteinaceous solutes. Ordinarily, an isolated agent will be prepared by at least one purification step. In one embodiment, the agent is purified to at least about 60%, at least about 65%, at least about 70%, at least about 75%, at least about 80%, at least about 85%, at least about 88%, at least about 90%, at least about 92%, at least about 95%, at least about 97%, at least about 98%, at least about 99%, at least about 99.9%, or at least about 99.99% by weight.

"Expressing" a protein in a cell means to ensure that the protein is present in the cell, e. g., for the purposes of a procedure of interest. In numerous embodiments, "expressing" a protein will comprise introducing a transgene into a cell comprising a polynucleotide encoding the protein, operably linked to a promoter, wherein the promoter is a constitutive promoter, or an inducible promoter where the conditions sufficient for induction are created, as well as a localization sequence. However, a cell that, e. g., naturally expresses a protein of interest, can be used without manipulation and is considered as "expressing" the protein. For the present invention, "specific expression of a depolarizing light-gated ion channel in a retinal photoreceptor" means that the depolarizing light-gated ion channel is expressed exclusively (more than 75%) in a retinal photoreceptor. It is important to note that an expression in many different cells might lead to contradictory signals, annihilating each other.

A "fluorescent probe" refers to any compound with the ability to emit light of a certain wavelength when activated by light of another wavelength.

"Fluorescence" refers to any detectable characteristic of a fluorescent signal, including intensity, spectrum, wavelength, intracellular distribution, etc.

"Detecting" fluorescence refers to assessing the fluorescence of a cell using qualitative or quantitative methods. For instance, the fluorescence is determined using quantitative means, e. g., measuring the fluorescence intensity, spectrum, or intracellular distribution, allowing the statistical comparison of values obtained under different conditions. The level can also be determined using qualitative methods, such as the visual analysis and comparison by a human of multiple samples, e. g., samples detected using a fluorescent microscope or other optical detector (e. g., image analysis system, etc.) An "alteration" or "modulation" in fluorescence refers to any detectable difference in the intensity, intracellular distribution, spectrum, wavelength, or other aspect of fluorescence under a particular condition as compared to another condition. For example, an "alteration" or "modulation" is detected quantitatively, and the difference is a statistically significant difference. Any "alterations" or "modulations" in fluorescence can be detected using standard instrumentation, such as a fluorescent microscope, CCD, or any other fluorescent detector, and can be detected using an automated system, such as the integrated systems, or can reflect a subjective detection of an alteration by a human observer.

An assay performed in a "homogeneous format" means that the assay can be performed in a single container, with no manipulation or purification of any components being required to determine the result of the assay, e. g., a test agent can be added to an assay system and any effects directly measured. Often, such "homogeneous format" assays will comprise at least one component that is "quenched" or otherwise modified in the presence or absence of a test agent.

Methods for expressing heterologous proteins in cells are well known to those of skill in the art, and are described, e. g., in Ausubel (1999), Guthrie and Fink (1991), Sherman, et al. (1982) Methods in Yeast Genetics, Cold Spring Harbor Laboratories, Freshney, and others. Typically, in such embodiments, a polynucleotide encoding a heterologous protein of interest will be operably linked to an appropriate expression control sequence for the particular host cell in which the heterologous protein is to be expressed. Any of a large number of well-known promoters can be used in such method. The choice of the promoter will depend on the expression levels to be achieved and on the desired cellular specificity. Additional elements such as polyadenylation signals, 5' and 3' untranslated sequences, etc. are also described in well-known reference books.

In metazoan (animals having the body composed of cells differentiated into tissues and organs) cells, promoters and other elements for expressing heterologous proteins are commonly used and are well known to those of skill. See, e. g., Cruz & Patterson (1973) Tissue Culture, Academic Press; Meth. Enzymology 68 (1979), Academic Press; Freshney, 3rd Edition (1994) Culture of Animal Cells: A Manual of Basic Techniques, Wiley-Liss. Promoters and control sequences for such cells include, e. g., the commonly used early and late promoters from Simian Virus 40 (SV40), or other viral promoters such as those from polyoma, adenovirus 2, bovine papilloma virus, or avian sarcoma viruses, herpes virus family (e. g., cytomegalovirus, herpes simplex virus, or Epstein-Barr Virus), or immunoglobulin promoters and heat shock promoters (see, e. g. Sambrook, Ausubel, Meth. Enzymology Pouwells, et al., supra (1987)). In addition, regulated promoters, such as metallothionein, (i. e., MT-1 and MT-2), glucocorticoid, or antibiotic gene "switches" can be used. Enhancer regions of such promoters can also be used.

Expression cassettes are typically introduced into a vector that facilitates entry of the expression cassette into a host cell and maintenance of the expression cassette in the host cell. Such vectors are commonly used and are well known to those of skill in the art. Numerous such vectors are commercially available, e. g., from Invitrogen, Stratagene, Clontech, etc., and are described in numerous guides, such as Ausubel, Guthrie, Strathem, or Berger, all supra. Such vectors typically include promoters, polyadenylation signals, etc. in conjunction with multiple cloning sites, as well as additional elements such as origins of replication, selectable marker genes (e. g., LEU2, URA3, TRP 1, HIS3, GFP), centromeric sequences, etc.

For expression in mammalian cells, any of a number of vectors can be used, such as pSV2, pBC12BI, and p91023, as well as lytic virus vectors (e. g., vaccinia virus, adenovirus, baculovirus), episomal virus vectors (e. g., bovine papillomavirus), and retroviral vectors (e. g., murine retroviruses).

As used herein, the term "disorder" refers to an ailment, disease, illness, clinical condition, or pathological condition.

As used herein, the term "pharmaceutically acceptable carrier" refers to a carrier medium that does not interfere with the effectiveness of the biological activity of the active ingredient, is chemically inert, and is not toxic to the patient to whom it is administered.

As used herein, the term "pharmaceutically acceptable derivative" refers to any homolog, analog, or fragment of an agent, e.g. identified using a method of screening of the invention, that is relatively non-toxic to the subject.

The term "therapeutic agent" refers to any molecule, compound, or treatment, that assists in the prevention or treatment of disorders, or complications of disorders.

Compositions comprising such an agent formulated in a compatible pharmaceutical carrier may be prepared, packaged, and labeled for treatment.

If the complex is water-soluble, then it may be formulated in an appropriate buffer, for example, phosphate buffered saline or other physiologically compatible solutions.

Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e. g., sorbitol syrup, cellulose derivatives or hydrogenated edible fats); emulsifying agents (e. g., lecithin or acacia); non-aqueous vehicles (e. g., almond oil, oily esters, or fractionated vegetable oils); and preservatives (e. g., methyl or propyl-p-hydroxybenzoates or sorbic acid). The pharmaceutical compositions may take the form of, for example, tablets or capsules prepared by conventional means with pharmaceutically acceptable excipients such as binding agents (e. g., pregelatinized maize starch, polyvinyl pyrrolidone or hydroxypropyl methylcellulose); fillers (e. g., lactose, microcrystalline cellulose or calcium hydrogen phosphate); lubricants (e. g., magnesium stearate, talc or silica); disintegrants (e. g., potato starch or sodium starch glycolate); or wetting agents (e. g., sodium lauryl sulphate). The tablets may be coated by methods well-known in the art.

The compounds may be formulated for parenteral administration by injection, e. g., by bolus injection or continuous infusion. Formulations for injection may be presented in unit dosage form, e. g., in ampoules or in multi-dose containers, with an added preservative.

The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e. g., sterile pyrogen-free water, before use.

The compounds may also be formulated as a topical application, such as a cream or lotion.

In addition to the formulations described previously, the compounds may also be formulated as a depot preparation. Such long acting formulations may be administered by implantation (for example, subcutaneously or intramuscularly) or by intramuscular injection.

Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the compositions in pharmaceutically acceptable form.

The composition in a vial of a kit may be in the form of a pharmaceutically acceptable solution, e. g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e. g., saline, dextrose solution, etc.), preferably sterile, to reconstitute the complex to form a solution for injection purposes.

In another embodiment, a kit further comprises a needle or syringe, preferably packaged in sterile form, for injecting the complex, and/or a packaged alcohol pad. Instructions are optionally included for administration of compositions by a clinician or by the patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Targeted expression of CatCh in cones from rd1 mice (mice homozygous for the rd1 mutation have an early onset severe retinal degeneration) was accomplished by the use of the cell-specific promoter mouse cone arrestin 3 (mCar) (Busskamp, 2010). This was previously shown to selectively drive expression in a high percentage of rd1 cones (Busskamp, 2010). CatCh, fused to enhanced green fluorescent protein, EGFP, was packaged inside AAVs and was injected into the subretinal space of rd1 mice. All mouse injections were performed between P28 and P39. EGFP only expressing AAVs were used as controls throughout the study. The ability of CatCh transfected rd1 cones to convey information to downstream retinal ganglion cells (RGCs), the output neurons of the retina, was measured on multielectrode arrays (MEA). Full field white light CatCh MEA recordings were performed between P79-P114. In CatCh transduced retinas robust RGC ON responses, both transient and sustained, were seen, starting at $10(15)$ effective photons per cm2 per sec. Responses persisted across four logarithmic units of light intensities. No light responses were elicited in rd1 mice injected with control EGFP only virus.

The cone can hence not only be made to hyperpolarize in response to light via e.g. halorhodopsin, mimicking the native hyperpolarizing opsin response. It can also be made to depolarize in response to light if CatCh is targeted to the rd1 cone.

Downstream of photoreceptors the retina segregates into two parallel information channels. ON bipolar and ON ganglion cells are activated by increments of light and are connected to cones via sign inverting synapses. OFF bipolar and OFF ganglion cells are activated by decrements of light and are connected to cones with sign conserving synapses. 7 Since CatCh transduced photoreceptors are now depolarizing in response to light, the ON pathway will hyperpolarize in response to light and will be silent while the OFF pathway will depolarize and will give rise to ON responses.

To demonstrate that depolarizing photoreceptors are able to transmit information to ganglion cells via inversion in both the ON and OFF circuitry, the inventors induced retinal degeneration in wild-type mice by introducing transgenes to their retina with a constitutive chicken β-actin (CBA) promoter. Ten days after subretinal injection of a AAV2/8-CBA-DIO-InhA-2A-EGFP cassette, the retina of wild type mice showed almost complete opsin. Cone arrestin labelling showed an alteration in cone morphology. Inner segments looked shortened, eventually disappearing altogether; cones were no longer sitting in the same photoreceptor layer plane and with time there was an apparent increase in cone cell body size. The inventors went on to co-inject this toxic CBA cassette with CatCh when wild type mice were P36. Full field white light MEA recordings were performed between P61-P73. Both ON and OFF ganglion cell responses were visible during MEA recordings.

The invention claimed is:

1. An isolated nucleic acid molecule comprising a nucleotide sequence, or a complementary nucleotide sequence thereof, and a promoter, wherein the nucleotide sequence codes for a depolarizing light-gated ion channel and is functionally linked to the promoter selected from the group consisting of SEQ ID NOs:1-6, wherein the promoter is capable of leading to specific expression of the depolarizing light-gated ion channel in a retinal photoreceptor.

2. The isolated nucleic acid molecule of claim 1, wherein the depolarizing light-gated ion channel is a channel rhodopsin.

3. The isolated nucleic acid molecule of claim 2, wherein the channel rhodopsin is channelrhodopsin-2 or a variant thereof.

4. The isolated nucleic acid molecule of claim 1, wherein the promoter is as set forth in SEQ ID NO:1.

5. The isolated nucleic acid molecule of claim 1, wherein the retinal photoreceptor cell is a rod or a cone.

6. A recombinant vector comprising the nucleic acid molecule of claim 1.

7. A host cell comprising the vector of claim 5.

8. The vector of claim 6, wherein the vector is a viral vector.

9. The vector of claim 8, wherein the viral vector is an adeno-associated viral (AAV) vector.

10. The isolated nucleic acid molecule of claim 1, wherein the promoter is selected from the group consisting of SEQ ID NO:2-6.

11. A kit for gene expression in retinal photoreceptors comprising the isolated nucleic acid molecule of claim 1.

12. The kit of claim 11, further comprising a needle or syringe and an instruction for administering the isolated nucleic acid molecule to a subject.

13. A method of treating or ameliorating blindness in a subject, wherein the method comprises administering to the subject a therapeutically effective amount of a nucleic acid molecule comprising a nucleotide sequence and a promoter, wherein the nucleotide sequence codes for a depolarizing light-gated ion channel and is functionally linked to the promoter selected from the group consisting of SEQ ID NOs:1-6, wherein the promoter is capable of leading to specific expression of the depolarizing light-gated ion channel in a retinal photoreceptor.

14. The method of claim 13, wherein the administering is performed through sub-retinal injection.

15. The method of claim 13, wherein the depolarizing light-gated ion channel is a channel rhodopsin.

16. The method of claim 7, wherein the promoter is as set forth in SEQ ID NO:1.

17. The method of claim 7, wherein the promoter is selected from the group consisiting of SEQ ID NO:2-6.

18. The method of claim 13, wherein the retinal photoreceptor cell is a rod or a cone.

19. A method of treating or ameliorating blindness in a subject, wherein the method comprises administering to the subject a therapeutically effective amount of a
    viral vector comprising a nucleic acid molecule,
    wherein said nucleic acid molecule comprises a nucleotide sequence and a promoter,
    wherein the nucleotide sequence codes for a depolarizing light-gated ion channel and is functionally linked to the promoter selected from the group consisting of SEQ ID NOs: 1-6, and
    wherein the promoter is capable of leading to specific expression of the depolarizing light-gated ion channel in a retinal photoreceptor.

20. The method of claim 19, wherein the administering is performed through sub-retinal injection.

21. The method of claim 20, wherein the viral vector is an AAV vector.

22. The method of claim 19, wherein the depolarizing light-gated ion channel is a channel rhodopsin.

23. The method of claim 19, wherein the promoter is as set forth in SEQ ID NO: 1.

24. The method of claim 19, wherein the promoter is selected from the group consisting of SEQ ID NO:2-6.

25. The method of claim 19, wherein the retinal photoreceptor cell is a rod or a cone.

* * * * *

SEQUENCE LISTING

```
<160> NUMBER OF SEQ ID NOS: 6

<210> SEQ ID NO 1
<211> LENGTH: 1229
<212> TYPE: DNA
<213> ORGANISM: Mus musculus

<400> SEQUENCE: 1
agctagcaca gcactaggct aaagcgtact gagcccttgt cttccgtggg agctgcagag      60
tgggatgcat gcgttgtgag ctgaggctca agctgcgctg gcagaagagc aggggttgcc    120
ttgtcagact ccagggtctc tttctctctg agcctgggaa agtgccactt tattggatct    180
ataaagccgg ggggggggg ggggaggaa tctcaaggtg aagaggaagt tcacagaccc    240
ctctaacgcc tctattagaa ccttccagct attctctcat acttgtacac tgagctggca    300
cacagtatag gcaagttcta ttcgcatcac ccctctagtt cctgtctccc tggttatgca    360
agcctcatat ttaggtagat gtgaccttag gaaaccaaaa tatcctttaa gatcttacta    420
actggttgcc tgttcagctt ttccacattg atcctgtagc cccctcgagg aggtgaagga    480
aaaaaatctc ctctttgttt ctctaactca ttaatgaatt ttaagggcac tctgtaaggt    540
tcctttccca ttctggtctg gttcgtacat tctgagaaac acactgtgtt tgtgttgaga    600
gttggctccc tagctacact gtctgtcaca ttgatgctct gagtagggac agggttcatc    660
taggaaatat attttcactc acactctgta tcttttccta gtttggcata ttctagtctg    720
catttggctc tctgtttaaa tataaaagaa aactaaaaca cacccttcag acgcctatgt    780
ctgaaaaatc tggcatttcc gtgggttttt cttaaggag gccttcattt gtaaccaaca    840
ccatgctctc cttaaggaaa tcaatctcaa tgccctatta tccttccctt ttctttcctc    900
ccagtttgag gctgcagttg cctttttttt tcttatcccc tgctgaacct gaaaaaccct    960
ctcttttcta cagttttctg ttcccaggcc ccgctgactt cctttagagc atgggggggg   1020
gggggatcag gattgtgatg tgtgaactgg gaggatcttg acctactccg ctaacccagt   1080
ggcctgagca aatcacaagg aggattggag ccatctgccc agccctccc ccacggcagc   1140 ctgctggaaa gagacaagtt agtcattcaa atgattggct ttttgcccgc ttcttctcta   1200 ataagaagg cagcagcttc tgctgaggt                                       1229

<210> SEQ ID NO 2
<211> LENGTH: 500
<212> TYPE: DNA
<213> ORGANISM: Mus musculus

<400> SEQUENCE: 2
```

```
catcctgaga gatgagccag acaaagaac cagtaatagc tcctggagca gcacatctgt      60
tttgccagga ttatcccttg atctcttaa accgagacc ttgtaatctg aagactcaac     120
ttgggctgta cccttaacct tcagctctat gatgcaagtg agtccacagg accggaggct    180
ttgagatgag cttttcagaa gggaggagtt ggccgcttgc tcccagagct ccagcacctg    240
cattcttctg gctatgtcag aagccagatc atttccctcg ttaaaaacaa aaacaaaaaa    300
acaaacaaac aaaatgttag tctttgccct ttatctgcct ggcaaagctt ttaattggct    360
tgatctgtca ttccgctaga cataaagggg acaatccccg gattaggaag gagctctcca    420
gctcgggtaa ggagtctcaa ggcaaggtag gcaagcacca ccggtccgca ctctcgccca    480
gcttttacgg gaagaagaga                                                500

<210> SEQ ID NO 3
<211> LENGTH: 2000
<212> TYPE: DNA
<213> ORGANISM: Mus musculus

<400> SEQUENCE: 3
agaggcaggc cgagtttgag gccagcctgg tctacacagg cgttctagga gaacctgtct     60
catatgcaca tgggcctggg attacacata caactgcaat ggcagcactt ggaaagcgga    120
agcaggagaa tcggaatttc acactcatcc ttcattatag aagtccaaac ctgtgctaag    180
ctacttggac atcgctaaaa aacagcaaaa atctttctag gaattgccaa tgtatacaca    240
ccaagttgta ttttgtagg gcagactttt ccaacttgcc agatgataat aatcatttat    300
attagctaca tttcaggctc cagaattaac actgttactg aaatgtatag gttctaaaac    360
ataccatttc caaatatttt aaaggattaa cattttgaa aagcatgtga tcttccaacc    420
atatttaggg gaacagacat aagaagtagg caagtttggg aagaaacagt tcctgagggc    480
atttcttccc aaccttgaat gccctgtggg ttaactgagg tcttggtaaa atgtagatta    540
tttactggac ttttgaact gagagtgcat ttctaacaaa actccagggt atgtggtcct    600
tgcattacat atggggtagc aacattctaa agcagtgttt ttcaacctgt ggatcaagac    660
ccacagaagt cacatagcag atatcctgcc tattagatat ttacattaag attcagagca    720
gtagcagaat aggagtcatc ccaacctgag gaactgcatc agagtcccag catcaggaag    780
ggtgagagcc actgagctaa agtcctctag gtgaggggc tgccccggaa agactcattt    840
aaatgaaacc actgacacag agagctgaca gatgaggtgg gttccgtgtc tgtgaggctc    900
tgctggtcgt ctcctcactc ccatggaaga accaccgaga tgagggcgag gggcagagct    960
aacccagcct ctaagtaggc agagtctagt gtccagctgc ccaaggaaga agtttgctgt   1020
gtgaggtggc cctgatgtcc gcacacacaa aatgccagtg aagtctactt gaccaagtga   1080
agctggtgtg gaatgggaag aagcacacac agtcagtctc tctgcacaca ctctgtcctt   1140
cacttcttca cttaccagag atttgatgag aacctactag cagatcagat ttgatccctg   1200
agtggaaaaa acgtacagtg ggagataaaa gaggaaaaca acggatctga gtttgaggtt   1260
agcctagtct gagcaagccg gatacacagt aagaccctgt ctcacataca tccactcgca   1320
cgcgcgcgca cacaaacaca cacacacaca cacacacaca cacacacaca cacacacatc   1380
gtgctaagga caagataggc atcctgagag atgagccagg acaaagaacc agtaatagct   1440
cctggagcag cacatctgtt ttgccaggat tatcccttgg atctcttaaa accgagacct   1500
tgtaatctga agactcaact tgggctgtac ccttaacctt cagctctatg atgcaagtga   1560
```

| | |
|---|---|
| gtccacagga ccggaggctt tgagatgagc ttttcagaag ggaggagttg gccgcttgct | 1620 |
| cccagagctc cagcacctgc attcttctgg ctatgtcaga agccagatca tttccctcgt | 1680 |
| taaaaacaaa aacaaaaaaa caaacaaaca aaatgttagt ctttgcccctt tatctgcctg | 1740 |
| gcaaagcttt taattggctt gatctgtcat tccgctagac ataaagggga caatccccgg | 1800 |
| attaggaagg agctctccag ctcgggtaag gagtctcaag gcaaggtagg caagcaccac | 1860 |
| cggtccgcac tctcgcccag cttttacggg aagaagagaa tgttactcta tcctaacata | 1920 |
| ttttttccttt tcctctatct cacagatagg aaaaatttaa gagccagagg gaacgtccct | 1980 |
| tctcagagga gacagcagaa | 2000 |

<210> SEQ ID NO 4
<211> LENGTH: 2000
<212> TYPE: DNA
<213> ORGANISM: Mus musculus

<400> SEQUENCE: 4

| | |
|---|---|
| ctctcctccc attgatgact gactaggcca tcctctgcta cataggtggc tggagcctga | 60 |
| gtccctcctt gtgtactctt tggttggtgg tttactctgg gggtactggt tagttcgtat | 120 |
| tgttgttcct cctaggggac tgcaaacccc ttcagctcct tgggtccttt ctctagttcc | 180 |
| ttctttgggg accctgtgct cagttcaatg gatggccaat ttccttctta aatgccccta | 240 |
| gcagtaactg ttaggtctca atcccaagac aaatgtctga ggtgcctatt taacagatca | 300 |
| aagcggacct ggcctcaggt tatcccagtc cctccctgta cctcagtccc tacccatcac | 360 |
| caactctcca gcccagagct tgggctgcac ttcccccacg gttcttccca ttttggctac | 420 |
| atggtctttt ttttttacctt tttggttcct ttggcctttt ggcttttggc ttccagggct | 480 |
| tctggatccc ccccaacccc tcccatacac atacacatgt gcactcgtgc actcaaccca | 540 |
| gcacaggata atgttcattc ttgacctttc cacatacatc tggctatgtt ctctctctta | 600 |
| tctacaataa atctcctcca ctatacttag gagcagttat gttcttcttc tttctttctt | 660 |
| tttttttttt ttcattcagt aacatcatca gaatcccta gctctggcct acctcctcag | 720 |
| taacaatcag ctgatccctg gccactaatc tgtactcact aatctgttttt ccaaactctt | 780 |
| ggcccctgag ctaattatag cagtgcttca tgccacccac cccaacccta ttcttgttct | 840 |
| ctgactccca ctaatctaca cattcagagg attgtggata taagaggctg ggaggccagc | 900 |
| ttagcaacca gagctggagg ctgatgcgag cttcatctct tccctcaggt aatattctaa | 960 |
| atctctctgc ttctagccca tactaagtcc acctcctttg cctttagcat cttctttagg | 1020 |
| aggagagggg catcttttct gatgcaagca atggattttt caggctgatg taagagactt | 1080 |
| ctagaactca gcaccccccc ccaactcatc cctctgacca agcctactat gttttgaagg | 1140 |
| aaagcaccag aaagacattt ccctctctat gcttccctag caccttaagc gtggggacag | 1200 |
| gatggaaatg tttggggaaa gtgacaagag agatgatgag taagggcaaa gagggctttc | 1260 |
| ggcctccaca gaggcttcta ctgccacccc ccaagaaagt atgagcgcaa ccctttctgt | 1320 |
| tctacagctt tccctcttct ttcccccacc tcccccctgt tcttccttct gagctggagg | 1380 |
| tcaaaagcat cccaattcag ggtcaagtcc agtacaggga caaaaagaaa tttcatccat | 1440 |
| tcatttattt attcatatag ttaactgact gtgtgcctgt tgaagttcag tatcaatgca | 1500 |
| gcccaaggaa cgtatttaag agatggagta tgagcaagta ggataaatag aaggggttaa | 1560 |
| aaaataagat gaggagcaat caagaaagac actggacatt cctctagctt tcacacacat | 1620 |
| gcacctgtgc atgcatggat acatgcacag gcattcgctc atgcacatac acatgagaga | 1680 |

```
gagagagaat gagagagaga gagagagaga gagagagaga gagagagaga gagagagaga      1740
gagagagaga gaaagagaga aagagagaaa gagagaaaga gaatgtagtg caatggttgg      1800
gtaagtgtgt aactgaagag ttgccctaag aagaggaaaa aaaaaaagga agcattgagt      1860
gttggtgtgg tatctcaggc agttaattta tattcacta ggtgtatcat tatggaatat       1920
tatagtgcac taaaaaaaaa aggattaaat aactgagtgt tcctcttccc ctcatctcag      1980
gaaagattca actggccagc                                                  2000

<210> SEQ ID NO 5
<211> LENGTH: 734
<212> TYPE: DNA
<213> ORGANISM: Mus musculus

<400> SEQUENCE: 5
agatctatta gtaaaattaa ctacacctgg tcctttatgt cattaactac acgtcagtcg       60
ttctattatt aactcacag aacttactat ataattaact acaccgcgca tttggatata      120
ttaactacac aactttgctt aataaattaa ctacacccgt aacggattct cattaactac      180
acgtttcatt acgagggatt aactacacat agccccggga ggcattaact acacttttg      240 aggtcgcgaa ttaactacac ttcgactcgc aggacattaa ctacactata ccgataacgc      300
aattaactac acaaattttt tatgaagatt aactacactg ttcgctcctg cctattaact      360
acacgaggcc gtatttccaa ttaactacac ccgagacaca agataattaa ctacacttaa      420
ccagatggca gattaactac acgtacgggc aggcccgatt aactacaccg gctgtcattc      480
ctcattaact acacatatca cgacttgtga ttaactacac gctcgagatc tgcgatctgc      540
atctcaatta gtcagcaacc atagtcccgc ccctaactcc gcccatcccg cccctaactc      600
cgcccagttc cgcccattct ccgccccatc gctgactaat ttttttttatt tatgcagagg      660 ccgaggccgc ctcggcctct gagctattcc agaagtagtg aggaggcttt tttggaggcc      720
taggcttttg caaa                                                        734

<210> SEQ ID NO 6
<211> LENGTH: 774
<212> TYPE: DNA
<213> ORGANISM: Mus musculus

<400> SEQUENCE: 6
gtactgcgga catccgctaa ttagcataac ccgcaaggat gtagctaatt agcatatcac       60
gggagactgg ggctaattag cataaaaagt ctcccgcctg ctaattagca tacgagactc      120
tagaatcgct aattagcata tcagtcaaac cacttgctaa ttagcataag catcgcgcta      180
tttgctaatt agcataaatg ttacatacat cgctaattag catatgatag cactgtcaag      240
ctaattagca tatcagccgc acgcatggct aattagcata cgaataccac aagctgctaa      300
ttagcatacg gttaaaataa tacgctaatt agcatatcaa agacgacaga agctaattag      360
catagatcac catcaccacg ctaattagca tacgttaatg ctgttctgct aattagcata      420
gaaattgttg atctggctaa ttagcatacc cgccttcctg aacgctaatt agcatacggt      480
acgtcgagat tgctaattag catatgtact gaacccatag ctaattagca taataaatta      540
ctaatccgct aattagcata gctcgagatc tgcgatctgc atctcaatta gtcagcaacc      600
```

-continued

```
atagtcccgc ccctaactcc gcccatcccg cccctaactc cgcccagttc cgcccattct    660
ccgccccatc gctgactaat tttttttatt tatgcagagg ccgaggccgc ctcggcctct    720
gagctattcc agaagtagtg aggaggcttt tttggaggcc taggcttttg caaa          774
```